(12) United States Patent
Levy et al.

(10) Patent No.: US 6,893,639 B2
(45) Date of Patent: May 17, 2005

(54) METHOD FOR HIGH YIELD PURIFICATION OF IMMUNE GLOBULINS FROM BLOOD PLASMA AND BLOOD PLASMA INTERMEDIATES

(75) Inventors: Joshua Levy, North Hollywood, CA (US); Fred Rothstein, Long Beach, CA (US); Bahman Shimiaei, Los Angeles, CA (US)

(73) Assignee: Hemacare Corporation, Woodland Hils, CA (US)

( * ) Notice: Subject to any disclaimer, the term of this patent is extended or adjusted under 35 U.S.C. 154(b) by 0 days.

(21) Appl. No.: 10/041,950

(22) Filed: Oct. 19, 2001

(65) Prior Publication Data

US 2003/0078384 A1 Apr. 24, 2003

(51) Int. Cl.[7] .................... A61K 39/395; C07K 16/00
(52) U.S. Cl. .................... 424/176.1; 424/177.1; 530/390.1; 530/390.5; 530/414; 530/416; 530/419
(58) Field of Search .................... 424/176.1, 177.1; 530/390.1, 390.5, 414, 416, 419

(56) References Cited

U.S. PATENT DOCUMENTS

| | | |
|---|---|---|
| 4,082,734 A | 4/1978 | Stephan |
| 4,371,520 A | 2/1983 | Uemura et al. |
| 4,404,131 A | 9/1983 | Schwarz et al. |
| 4,481,189 A | 11/1984 | Prince |
| 4,762,714 A | 8/1988 | Mitra et al. |
| 4,877,866 A | 10/1989 | Rudnick et al. |
| 4,948,877 A | 8/1990 | Mitra et al. |
| 5,159,064 A | 10/1992 | Mitra et al. |
| 5,419,906 A | 5/1995 | Mitra et al. |
| 5,648,472 A * | 7/1997 | Gehringer et al. .......... 530/412 |
| 5,886,154 A | 3/1999 | Lebing et al. |
| 6,093,324 A * | 7/2000 | Bertolini et al. ............ 210/635 |
| 6,096,872 A | 8/2000 | Van Holten et al. |
| 6,162,904 A * | 12/2000 | Mamidi et al. .......... 530/390.1 |
| 6,307,028 B1 * | 10/2001 | Lebing et al. ........... 530/390.1 |

FOREIGN PATENT DOCUMENTS

WO     WO 99/33484     7/1999

OTHER PUBLICATIONS

L. Martinache and M.P. Henon.: "oncentration and Desalting by Ultrafiltration." Methods Plasma Protein Fractionation, 1980, pp. 223–235, PCT.

K. Tanaka, E. Sawatani, G.A. Dias, E.M. Shigueoka, T.C.X.B. Campos, H.C. Nakao and F. Arashiro, "High Quality Human Immunoglobulin G Purified from Cohn Fractions by Liquid Chromatography." Brazilian Journal of Medical and Biological Research, Jan. 2000, vol. 33, No. 1, pp. 27–30, Sao Paulo, SP, Brasil.

* cited by examiner

Primary Examiner—David Saunders
(74) Attorney, Agent, or Firm—Fulwider Patton Lee & Utecht, LLP

(57) ABSTRACT

The method for immune serum globulin purification relates to the purification of immune globulins from blood plasma with a high degree of efficiency and a high rate of recovery. The immune globulin source is Cohn's fraction I+II+III or II+III prepared from plasma or plasma intermediates by precipitation of the paste at pH 5.7 to 5.8 in the presence of 20% ethanol and 80% purified water. A glycine extraction is followed by an anion exchange chromatography column step to achieve a significantly high yield and high purity of the concentrated protein.

38 Claims, 1 Drawing Sheet

HIGH YIELD PURIFICATION OF IMMUNE GLOBULINS FROM PLASMA

PROCESS FLOW-CHART

METHOD FOR HIGH YIELD PURIFICATION OF IMMUNE GLOBULINS FROM BLOOD PLASMA AND BLOOD PLASMA INTERMEDIATES

BACKGROUND OF THE INVENTION

This invention relates generally to immune serum globulin purification, and more particularly concerns a method of purification of immune globulins from blood plasma with a high degree of efficiency and a high rate of recovery.

Blood plasma proteins have been purified for their therapeutic values for several decades. The most popular method of protein purification with wide industrial application was invented by Dr. Edwin J. Cohn. Dr. Cohn's method uses cold alcohol fractionation to separate major protein components of plasma. With the advent of new technologies, the present invention significantly improves on the recovery and purity of proteins from blood plasma.

It is desirable to provide a method for producing a higher yield of purified immune globulins from blood plasma, with fewer process steps and an increased recovery of the final product. The reduction in the number of process steps and duration of processing will further assure the structural integrity of the original molecules as the native proteins. The present invention meets these needs and others.

SUMMARY OF THE INVENTION

Briefly, and in general terms, the present invention provides a method for purification of immune globulins from blood plasma with a high degree of efficiency and a high rate of recovery. The method of the present invention differs from prior protein purification/recovery methods in that it combines a glycine extraction followed by an anion exchange chromatography column step to achieve a significantly high yield and high purity of the concentrated protein.

The invention is directed to a method for producing a high yield of purified immune globulins from blood plasma. In a preferred embodiment, the method involves suspension of blood product intermediates or any other biologic source containing immune globulins (or antibodies) in a solution containing about 20% ethanol and about 80% distilled water (volume/volume) with pH adjusted to between 5.7 and 5.8 and a temperature of about −5° C. The suspension is either precipitated to remove the lipid-containing supernatant (or filtrate) or is incubated at the said temperature before proceeding to the next step. The precipitate or the suspension is then brought to a concentration of 15% ethanol (volume/volume) and about 0.8M glycine at pH 5.2 to 5.4 and at a temperature of approximately −3° C. The solution is incubated at the above conditions to facilitate the extraction of immune globulins (or antibodies) by the glycine solution. Liquid-solid separation is performed to extract the immune globulins in the liquid phase. The liquid phase is then concentrated and solvent-exchange is performed to reduce the glycine and alcohol content. The protein solution is then loaded onto an anion exchange column to bind and reduce any protein impurities. The column flow-through that contains the immune globulins (or antibodies) is then concentrated to approximately 6% protein content. The inactivation of viruses which may be present in the concentrated protein solution is performed by a method of choice. The preferred method of viral inactivation is the solvent-detergent method in accordance with U.S. Pat. No. 4,481,189 (Prince). The solvent-detergent is removed from the protein solution by adsorption onto a C-18 resin column. The collected protein is formulated for final use in a liquid or as a freeze-dried preparation. Preferably, the collected protein is in the liquid formulation wherein the final concentration is adjusted to approximately 5.0 to 10.0 grams/deciliter protein, in 0.1% Tween-80, 0.2M glycine and pH between 8.2 and 8.6.

These and other aspects and advantages of the invention will become apparent from the following detailed description, which illustrates by way of example the features of the invention.

DETAILED DESCRIPTION OF THE PREFERRED EMBODIMENTS

Figure 1:
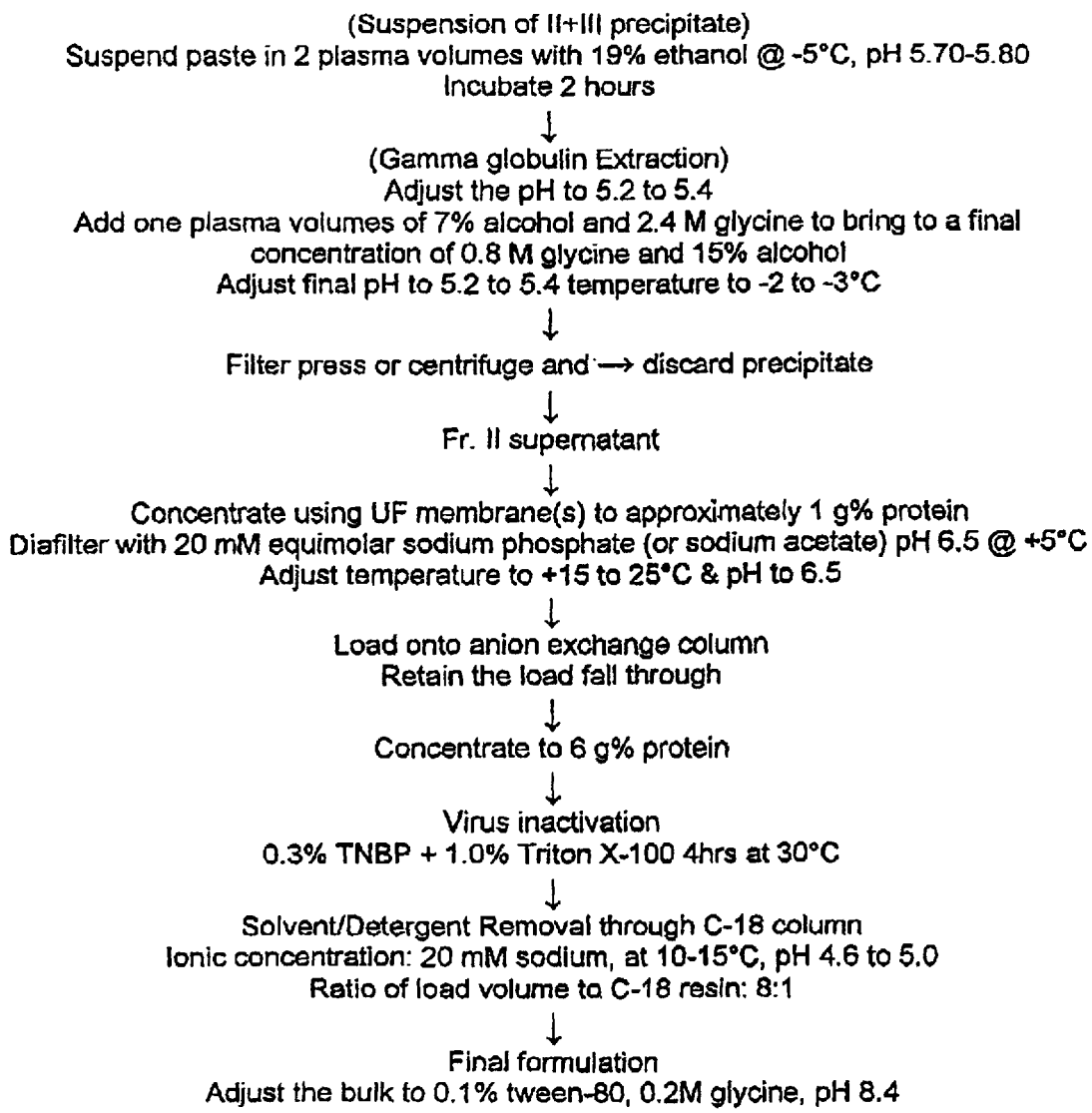
FIG. 1 is a flow-chart of a method for high yield purification of immune globulins from blood plasma in accordance with the present invention.

This improved method of the present invention ensures a high yield and high purity preparation of immune globulins from human plasma or similar immune globulin sources. The overall recovery of immune globulins from Cohn fraction II+III or I+II+III is about 80% with a purity of 99% or more as measured by zone electrophoresis. The final product of the concentrated protein is stable and has low anti-complement activity.

The conventional industrial methods of immune globulins purification from blood plasma are based on cold ethanol fractionation which co-precipitated groups of proteins based on their isoelectric points at given alcohol concentrations at sub-zero temperatures. Use of the glycine extraction method in the present invention, followed by chromatographic separation, combines the benefits of a crude protein cut, followed by a specific purification over the chromatography column.

In a preferred embodiment, the immune globulin source is Cohn's fraction I+II+III or II+III prepared from plasma or plasma intermediates by precipitation of the paste at pH 5.7 to 5.8 in the presence of 20% ethanol and 80% purified water. As shown in FIG. 1, the immune globulin (or antibody) source, Cohn's fraction I+II+III or II+III, is suspended in a solution consisting of about 19% ethanol and about 81% purified water at a volume equivalent to two times that of the initial source at a temperature in a range of about −4° C. to about −6° C. with vigorous agitation. It is preferred that the immune globulin suspension is prepared at a temperature of approximately −5° C. Alternative sources of immune globulins or antibodies can be derived from non-human sources such as those from tissue culture or animal origin for use in the present invention.

The precipitation of a majority of phospholipids from the immune globulin suspension is activated by adjusting the pH of the suspension to approximately 5.7 to 5.8 using 1.0M sodium acetate (or 4.0M sodium acetate for less volume) while continuously agitating the suspension. The suspension is incubated for a minimum of two hours at a temperature in a range of about −4° C. to about −6° C. with moderate agitation. Alternatively, liquid-separation of the suspension can be performed at this step in the process, rather than incubation of the suspension, followed by repetition of the earlier steps of preparing the suspension and precipitating the same.

Following the incubation period of the immune globulin suspension, a volume of a solution of 2.4M glycine in 7% ethanol and purified water (volume/volume), equivalent to the volume of the initial plasma source, is added to the suspension with vigorous mixing. Preferably, the final concentration of alcohol in the suspension is 15% (volume/volume) and the final concentration of glycine in the suspension is 0.8M. In order to have a better separation and higher yield, the volume of the suspension can be increased to a volume equivalent to five times the volume of the initial plasma source while maintaining the ethanol and glycine at 15% and 0.8M respectively. The pH of the suspension is then preferably adjusted to about 5.2 to about 5.4 using a buffer of 1.0M to 4.0M sodium acetate. The suspension temperature is raised to approximately −2° C. to −3° C.

The preferred technique for this separation is by use of a filter press. Filtration is facilitated with the use of diatomaceous earth at a concentration in a range of about 1% to 3% (weight/volume).

The filtrate or the centrifugate is then concentrated preferably by ultrafiltration to approximately 1.0 gram/deciliter protein content at a temperature in a range of about −2° C. to about −3° C. with moderate agitation. Ultrafiltration of the filtrate or the centrifugate containing the immune globulins is performed preferably by using a 100,000 molecular weight cut-off ultrafilter membrane to concentrate the protein to approximately 1 g %.

In order to reduce the glycine and alcohol content of the protein concentrate, solvent-exchange is performed using a solution of 20 mM sodium phosphate at a pH of about 6.5 and a temperature of about 5° C. The solution is prepared by a mixture of sodium phosphate monobasic and sodium phosphate dibasic at a ratio that yields a pH of about 6.5. Alternatively, a buffer consisting of 20 mM sodium acetate at a pH of about 6.5 can be used in the present invention. Solvent-exchange is performed by adding one volume of the pH 6.5 buffer to the protein concentrate and concentrating the new solution to its original volume. The solvent-exchange procedure is performed at least four times in order to ensure a reduction in the alcohol and glycine content of the protein concentrate. Following the last solvent-exchange, the temperature of the protein solution is raised to room temperature (15° C. to 25° C.).

The protein solution is then preferably passed through an anion exchange chromatography column to remove any impurities such as IgA, IgM, albumin and other protein impurities. Examples of the type of gel (resin) that can be used in the present invention to achieve satisfactory purification results includes a Pharmacia Q-Sepharose gel (resin). The column is equilibrated with the same 20 mM, pH 6.5 buffer that was used for solvent-exchange. The column is post-washed with one to two column volumes of the 20 mM, pH 6.5 buffer for any further recovery of protein. The ratio of the protein to the gel is approximately 0.4 grams of protein/milliliter of packed gel. The column effluent that contains the purified immune globulins or antibodies is concentrated by ultrafiltration to approximately 6 grams/deciliter protein content (6 g %) using a 100,000 molecular weight cut-off ultrafilter membrane.

After concentrating the column effluent by ultrafiltration, viral inactivation is performed on the concentrated protein solution. A preferred method of viral inactivation is the solvent-detergent method in accordance with U.S. Pat. No. 4,481,189 (Prince). The mixture of the solvent-detergent and protein concentrate consists of a final concentration of 0.3% TNBP (tri-n-butyl phosphate) and 1.0% Triton-X-100 and is then incubated for approximately four hours at 30° C. Following incubation of the combined protein concentrate and solvent-detergent mixture, the solvent-detergent is removed from the protein solution by adsorption onto a C-18 resin. The pH of the protein solution is then adjusted to about 4.6 to about 5.0 using a buffer of 4.0M sodium acetate. The column containing the C-18 resin is equilibrated with a 20 mM acetate buffer at a pH in a range of about 4.6 to about 5.0. The protein solution is loaded onto and passed through the column in order to remove the remaining solvent-detergent from the viral inactivation procedure. The ratio of the load volume to the resin volume is approximately eight parts load volume to one part C-18 resin.

The collected protein from the column is formulated for final use either in a liquid or as a freeze-dried preparation. Preferably, the final product is in a liquid formulation having a concentration of approximately 5.0 to 10.0 grams/deciliter protein, 0.1% polysorbate-80 (Tween-80), 0.2M glycine and a pH in a range of about 8.2 to about 8.6.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for producing a high yield of purified immune globulins from blood plasma, comprising:

providing a plasma source containing immune globulins;

suspending the immune globulins in an ethanol solution at a volume equivalent to two times that of the plasma source at a temperature in a range of about −4° C. to −6° C.;

adjusting the pH of the suspension to about 5.7 to 5.8;

incubating the suspension for at least two hours;

adding a volume of a solution of about 2.4M glycine in about 7% ethanol and purified water (volume/volume) equivalent to the volume of the plasma source to the suspension;

adjusting the pH of the suspension to about 5.2 to 5.4;

extracting the immune globulins from the suspension in a liquid phase to provide an extract containing immune globulins;

concentrating the extract containing immune globulins by ultrafiltration of the extract containing immune globulins to provide an immune globulin solution of approximately 1.0 gram/deciliter immune globulins content;

performing solvent-exchange on the immune globulin solution with a sodium phosphate solution to provide an extract solution containing immune globulins;

removing any impurities from the extract solution containing immune globulins using an anion exchange chromatography column to provide a purified extract solution containing immune globulins;

concentrating the purified extract solution containing immune globulins deriving from an effluent of the anion exchange chromatography column by ultrafiltration to provide a concentrated purified extract solution containing immune globulins;

inactivating viruses present in the concentrated purified extract solution containing immune globulins;

passing the concentrated purified extract solution containing immune globulins through a column containing C-18 resin for removal by adsorption of any residue in the concentrated purified extract solution containing immune globulins from the step of inactivating viruses, wherein the ratio of immune globulins load volume to resin volume is approximately eight parts load volume to one part C-18 resin; and formulating the concentrated purified extract solution containing immune globulins for final use.

2. The method of claim 1, wherein the plasma source containing immune globulins is selected from the group consisting of a Cohn fraction II+III and a Cohn fraction I+II+III.

3. The method of claim 1, wherein the ethanol solution is comprised of about 19% ethanol and about 81% purified water adjusted to a pH of 5.7 to 5.8.

4. The method of claim 1, wherein the step of suspending the immune globulins in the ethanol solution comprises vigorously agitating the plasma source.

5. The method of claim 1, wherein the step of suspending the immune globulins in the ethanol solution occurs at a temperature of about −5° C.

6. The method of claim 1, wherein the plasma source containing immune globulins is derived from human blood plasma.

7. The method of claim 1, wherein the plasma source containing immune globulins is derived from a non-human source.

8. The method of claim 1, wherein the volume of the immune globulins suspension increases to a volume equivalent to three times that of the plasma source to enhance protein recovery.

9. The method of claim 1, wherein the plasma source contains phospholipids.

10. The method of claim 9, wherein step of adjusting the pH of the suspension comprises adding 1M sodium acetate to effect precipitation of a majority of the phospholipids as the suspension is continuously agitated.

11. The method of claim 9, wherein the step of adjusting the pH of the suspension comprises adding 4M sodium acetate to effect precipitation of a majority of the phospholipids as the suspension is continuously agitated.

12. The method of claim 1, wherein the step of incubating the suspension for at least two hours comprises moderately agitating the suspension.

13. The method of claim 1, wherein the step of adding the solution of glycine and ethanol to the suspension comprises vigorously mixing the suspension.

14. The method of claim 1, wherein the step of adding the solution of glycine and ethanol to the suspension comprises producing a final concentration of glycine in the suspension of about 0.8M and a final concentration of ethanol in the suspension of about 15% (volume/volume).

15. The method of claim 1, wherein the step of adjusting the pH of the suspension to about 5.2 to 5.4 further comprises increasing the suspension temperature to approximately −2° C. to −3° C.

16. The method of claim 1, wherein the step of extracting the immune globulins from the suspension is performed by one of centrifugation and filtration.

17. The method of claim 1, wherein the step of extracting the immune globulins from the suspension is performed by use of a filter press.

18. The method of claim 1, wherein the step of extracting the immune globulins from the suspension is facilitated using diatomaceous earth at a concentration of about 1% to about 3% weight by volume during filtration.

19. The method of claim 1, wherein the step of extracting the immune globulins from the suspension is performed at a temperature in a range of about −2° C. to −3° C. while moderately agitating the suspension.

20. The method of claim 1, wherein the extract containing immune globulins is concentrated by ultrafiltration at a temperature in a range of about −2° C. to −3° C. while moderately agitating the extract containing immune globulins.

21. The method of claim 1, wherein the extract containing immune globulins is concentrated through an ultrafilter membrane having a molecular weight cut off of about 100,000.

22. The method of claim 1, wherein the step of performing solvent-exchange is performed using a solution of about 20 mM sodium phosphate at a temperature of about 5° C. and a pH of about 6.5.

23. The method of claim 1, wherein the step of performing solvent-exchange is performed using a solution of sodium phosphate prepared by mixing sodium phosphate monobasic and sodium phosphate dibasic at a ratio that yields a pH of about 6.5.

24. The method of claim 1, wherein the step of performing solvent-exchange is performed using a solution of about 20 mM sodium acetate at a pH of about 6.5.

25. The method of claim 1, wherein the step of performing solvent-exchange is performed by addition of one volume of the pH 6.5 buffer to the immune globulins solution forming the extract solution containing immune globulins and concentrating the extract solution containing immune globulins to its original volume.

26. The method of claim 1, wherein the step of performing solvent-exchange is performed approximately four times to reduce the alcohol and glycine content.

27. The method of claim 26, further comprising increasing the temperature of the immune globulins solution to room temperature at 15° C. to 25° C. after approximately the fourth solvent-exchange.

28. The method of claim 1, wherein the anion exchange chromatography column is equilibrated with a 20 mM sodium phosphate buffer at a pH of about 6.5.

29. The method of claim 28, wherein the anion exchange chromatography column is washed with at least one column volume of the 20 mM buffer after passing the extract solution containing immune globulins therethrough to obtain further immune globulins recovery.

30. The method of claim 1, wherein the anion exchange chromatography column is packed with a gel, and a ratio of immune globulins to the gel is approximately 0.4 grams of protein/milliliter of gel.

31. The method of claim 1, wherein the purified extract solution containing immune globulins is concentrated from the column effluent to approximately 6 grams/deciliter immune globulins using an ultrafilter membrane having a molecular weight cut off of about 100,000.

32. The method of claim 1, wherein a solvent-detergent method is used for inactivating viruses present in the concentrated purified extract solution containing immune globulins.

33. The method of claim 32, wherein a mixture of the purified extract solution containing immune globulins and solvent-detergent yields a final concentration of 0.3% TNBP (tri-n-butyl phosphate) and 1.0% Triton-X-100 and is incubated for about four hours at about 30° C.

34. The method of claim 1, wherein the step of passing the concentrated purified extract solution containing immune globulins through a column containing C-18 resin for removal of remaining residue further comprises adjusting the pH of the concentrated purified extract solution containing immune globulins to about 4.6 to about 5.0 with a 4.0M sodium acetate buffer.

35. The method of claim 1, wherein the column containing the C-18 resin is equilibrated with a 20 mM sodium acetate buffer at a pH of about 4.6 to about 5.0.

36. The method of claim 1, wherein the concentrated purified extract solution containing immune globulins is formulated for final use in one of a liquid and a freeze-dried preparation.

37. The method of claim 36, wherein the concentrated purified extract solution containing immune globulins is a liquid preparation with a formulation wherein the concentration of the immune globulins is adjusted to a range of about 5.0 to about 10.0 grams/deciliter protein, 0.1% polysorbate-80 (Tween-80), 0.2M glycine, and pH in a range of about 8.2 to about 8.6.

38. A method for producing a high yield of purified immune globulins from blood plasma, comprising:

providing a plasma source containing immune globulins;

suspending the immune globulins in an ethanol solution at a volume equivalent to two times that of the plasma source at a temperature in a range of about −4° C. to −6° C.;

adjusting the pH of the suspension to about 5.7 to 5.8;

adding a volume of a solution of about 2.4M glycine in about 7% ethanol and purified water (volume/volume) equivalent to the volume of the plasma source to the suspension;

extracting the immune globulins from the suspension in a liquid phase to provide an extract containing immune globulins;

concentrating the extract containing immune globulins to provide an immune globulin solution of approximately 1.0 gram/deciliter immune globulins content;

performing solvent-exchange on the immune globulin solution with a sodium phosphate solution to provide an extract solution containing immune globulins;

removing impurities from the extract solution containing immune globulins using an anion exchange chromatography column to provide a purified extract solution containing immune globulins;

concentrating the purified extract solution containing immune globulins deriving from an effluent of the anion exchange chromatography column to provide a concentrated purified extract solution containing immune globulins to provide a concentrated purified extract solution containing immune globulins;

inactivating viruses present in the concentrated purified extract solution containing immune globulins;

passing the concentrated purified extract solution containing immune globulins through a column containing C-18 resin for removal by adsorption of any residue in the concentrated purified extract solution containing immune globulins from the step of inactivating viruses, wherein the ratio of immune globulins load volume to resin volume is approximately eight parts load volume to one part C-18 resin; and formulating the concentrated purified extract solution containing immune globulins for final use.

* * * * *